US008193173B2

(12) United States Patent
Hasumi et al.

(10) Patent No.: US 8,193,173 B2
(45) Date of Patent: Jun. 5, 2012

(54) LIVER FUNCTION AMELIORANT

(75) Inventors: Keiji Hasumi, Tokyo (JP); Fumihiko Maeda, Tokyo (JP); Kunitoshi Mitsumori, Tokyo (JP)

(73) Assignee: Tokyo University of Agriculture and Technology TLO Co., Ltd., Tokyo (JP)

( * ) Notice: Subject to any disclaimer, the term of this patent is extended or adjusted under 35 U.S.C. 154(b) by 359 days.

(21) Appl. No.: 11/628,841

(22) PCT Filed: Feb. 17, 2006

(86) PCT No.: PCT/JP2006/302796

§ 371 (c)(1), (2), (4) Date: Dec. 8, 2006

(87) PCT Pub. No.: WO2007/094071

PCT Pub. Date: Aug. 23, 2007

(65) Prior Publication Data

US 2008/0293799 A1 Nov. 27, 2008

(51) Int. Cl.
*A61K 31/33* (2006.01)

(52) U.S. Cl. ........................................ 514/183

(58) Field of Classification Search .................. 514/183
See application file for complete search history.

(56) References Cited

U.S. PATENT DOCUMENTS 5,703,048 A * 12/1997 Roos et al. .................... 514/12
6,133,279 A 10/2000 Cynshi et al.
6,406,745 B1 * 6/2002 Talton ........................ 427/213

FOREIGN PATENT DOCUMENTS

| | | | |
|---|---|---|---|
| EP | 1944027 | A1 | 7/2008 |
| JE | 53-79035 | A | 7/1978 |
| JP | 53-99314 | A | 8/1978 |
| JP | 5-170769 | A | 7/1993 |
| JP | 10-72458 | A | 3/1998 |
| JP | 2002-065288 | A | 3/2002 |
| JP | 2004-224737 | A | 8/2004 |
| JP | 2004-224738 | A | 8/2004 |
| WO | WO-2007/040082 | A1 | 4/2007 |

OTHER PUBLICATIONS

English Translation of JP 2002-065288A, Hasumi et al.*

Han, H. 'Targeted Prodrug Design to Optimize Drug Delivery' AAPS Pharmsci, 2(1), Article 6, p. 1-11, 2000.*

Iida et al., "Rai BSA Jin'en ni Taisuru Kohotaizai, K-76COONa No. Eikyo" Saishin Igaku vol. 38, No. 8, 1983, pp. 1656-1661, Section III, particularly III Kosatsu no Ko, with English-language translation.

International Search Report for WO-2007/040082-A1 which issued on Nov. 14, 2006.

Extended European Search Report dated Jun. 11, 2010 in Application No. EP 06713937.8.

Lirussi, Flavio et al., "Current and future therapy of chronic hepatitis," Pharmacotherapy of Gastrointestinal Inflammation, pp. 51-75, XP009134411, Jan. 1, 2004.

* cited by examiner

*Primary Examiner* — Brandon Fetterolf
*Assistant Examiner* — Christopher R Stone
(74) *Attorney, Agent, or Firm* — Birch, Stewart, Kolasch & Birch, LLP

(57) ABSTRACT

The present invention relates to a liver function ameliorant containing orniplabin as an active ingredient thereof.

3 Claims, 2 Drawing Sheets

LIVER FUNCTION AMELIORANT

TECHNICAL FIELD

The present invention relates to a liver function ameliorant containing orniplabin as an active ingredient thereof.

BACKGROUND ART

Orniplabin is a triprenylphenol compound derived from the fungus, *Stachybotrys microspora*, and is known to have action which promotes plasminogen activation (Japanese Unexamined Patent Publication No. 2004-224737). More specifically, orniplabin binds to the fibrolysis factor, plasminogen, and alters its conformation to promote conversion of plasminogen to plasmin by plasminogen activator. In addition, orniplabin promotes binding of plasminogen to fibrin. Orniplabin also promotes dissolution of pulmonary embolisms thrombus in pulmonary embolism model rats in vivo.

However, actions of orniplabin other than the plasminogen activating action thereof have heretofore been unknown.

DISCLOSURE OF THE INVENTION

An object of the present invention is to provide a novel liver function ameliorant.

As a result of conductive extensive studies to solve the aforementioned problems, the inventors of the present invention found out that orniplabin is able to improve disorder of liver functions, thereby leading to completion of the present invention.

Thus, the present invention relates to a liver function ameliorant containing orniplabin as an active ingredient thereof, the use of orniplabin for production a liver function ameliorant, and a method for improving liver function comprising the administration of orniplabin.

Orniplabin has the chemical structure shown below.

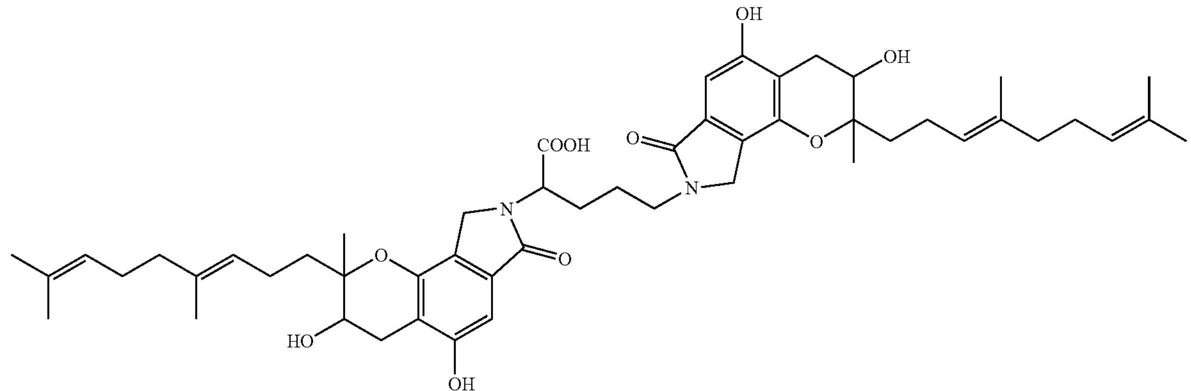

Although the above compound can be converted to a salt, preferable examples of such salts include alkaline metal or alkaline earth metal salts such as sodium salts, potassium salts, magnesium salts or calcium salts, and salts of organic bases such as triethylamine salts or trimethylamine salts, and these salts are also included in the present invention. In addition, salts in the manner of hydrates and solvates are also included in the present invention. Moreover, a compound of the present invention can also be used in the form of an ester. For example, an alcohol or carboxylic acid having 1 to 10 carbon atoms, and preferably methyl alcohol, ethyl alcohol, acetic acid or propionic acid, is preferable for forming a pharmaceutically acceptable ester of a compound of the present invention.

Orniplabin is a metabolite of filamentous bacteria such as *Stachybotrys* species, and can be prepared by culturing these strains.

More specifically, a filamentous bacterium such as a member of the genus *Stachybotrys* is selected for the producing organism, and preferably a filamentous bacterium of the genus *Stachybotrys* is selected. Although a particularly preferable producing organism is *Stachybotrys microspora* while *Stachybotrys microspora* strain IFO30018 is particularly preferable, the present invention is not limited to these bacteria.

Although any arbitrary medium can be used for the medium provided it is suitable for proliferation of the producing organism, Medium A is preferable. Medium A can be prepared by dissolving 20 g of glucose, 5 g of peptone, 3 g of yeast extract, 3 g of dibasic potassium phosphate and 1 g of magnesium sulfate heptahydrate in 1 liter of purified water, followed by adjusting the pH to 5.5 with hydrochloric acid or sodium hydroxide.

The most important aspect of the medium composition is the addition of ornithine to the medium. Although ornithine is preferably added to a concentration of 0.5 to 2 mg/ml, it is not limited to this concentration. Ornithine is preferably added during the period from immediately after culturing to day three of culturing. Although the culturing temperature is optimally 25° C., it is not limited thereto. A culturing time of 1 to 6 days after the addition of ornithine allows the obtaining of an adequate production volume. Suitable conditions for aeration and agitation are obtained by rotational culturing at 180 rpm in the case of placing 100 ml of Medium A in a 500 ml Erlenmeyer flask and using a suitable breathable plug. Equivalent conditions thereto are preferable in the case of using a jar fermenter.

The resulting compound can also be purified as necessary in accordance with ordinary methods such as column chromatography or silica gel chromatography.

Examples of the administration form of a compound of the present invention include oral administration by tablets, capsules, granules, powders or syrups, and parenteral administration by injection such as intravenous administration, subcutaneous administration or intraperitoneal administration, or by suppositories. These preparations can be produced by known methods using additives such as vehicles, binders, disintegration agents, lubricants, stabilizers and correctives.

Although varying according to the symptoms, age and so forth, the amount used is 0.01 to 100 mg/kg of body weight per day for normal adults, administered either once per day or divided into several administrations.

BEST MODE FOR CARRYING OUT THE INVENTION

Figure 1:
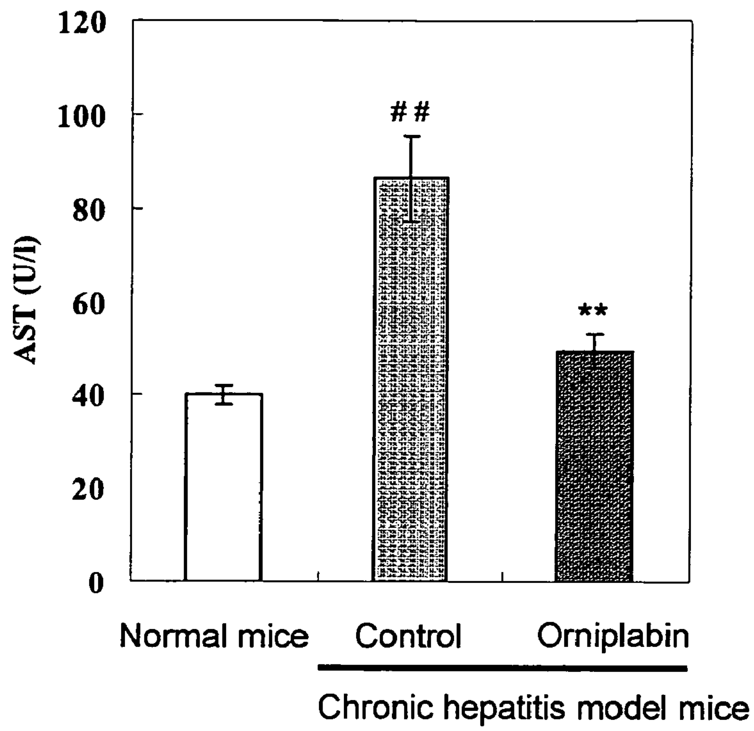
FIG. 1 shows the results of measuring plasma AST. The presence of significant differences between each group was tested using the Tukey multiple comparison test, and cases of a significant difference being observed at a level of significance of 0.01 with respect to a control group are indicated with two asterisks (**). In addition, cases of a significant difference being observed at a level of significance of 0.05 with respect to a normal group are indicated with a sharp mark (#), while cases of a significant difference being observed at a level of 0.01 with respect to a normal group are indicated with two sharp marks (##). The error bar indicates the standard error.

Although the following provides a more detailed explanation of the present invention through examples thereof, the present invention is not limited to the examples indicated below.

[Liver Function Ameliorative Effects in Chronic Hepatitis Model Mice]

(1) Production of Chronic Hepatitis Model Mice

Production of chronic hepatitis model mice was carried out according to a modified version of the method of Vogten et al. (J. Mathys Vogten et al., Int. J. Colorectal Dis. (2004), 19: 387-394).

ICR mice weighing about 30 g (age: 6 weeks, males, supplier: Sankyo Labo Service) were used in the experiment after preliminarily housing for 5 days while allowing free access to solid feed (Labo MR Stock) and distilled water. The animals were housed in an animal room set to conditions consisting of a temperature of 22±2° C., humidity of 60±5% and light-dark cycle of 12 hours.

Following preliminary housing, the animals were intraperitoneally administered carbon tetrachloride (10% corn oil solution (v/v)) three times a week. The initially dose was 330 μl/kg, the second dose was 400 μg/kg, and all subsequent doses were 500 μl/kg. This administration was carried out over the course of six weeks to produce chronic hepatitis model mice.

(2) Preparation of Orniplabin

Medium A was prepared by dissolving 20 g of glucose, 5 g of peptone, 3 g of yeast extract, 3 g of dibasic potassium phosphate and 1 g of magnesium sulfate heptahydrate in 1 liter of purified water followed by adjusting the pH to 5.5 with hydrochloric acid or sodium hydroxide. This Medium A was then placed in a 500 ml Erlenmeyer flask and sterilized by autoclaving for 15 minutes at 121° C. Medium A was then inoculated with *Stachybotrys microspora* strain IFO30018 and cultured for 4 days at 25° C. in a rotary shaker at 180 rpm. 1 ml of this culture liquid was then used as a seed culture liquid to inoculate a 500 ml Erlenmeyer flask containing 100 ml of Medium A prepared in the same manner. During this inoculation, L-ornithine was added to a concentration of 1 mg/ml. This was then cultured for 4 days at 25° C. in a rotary shaker at 180 rpm. Orniplabin (SMTP-7) had accumulated to a concentration of 305 μg/ml in this culture filtrate. After adjusting the pH of 3 liters of the culture filtrate to 3 with hydrochloric acid, 2.7 liters of methyl ethyl ketone were added to extract the orniplabin. This solvent extract was then concentrated to a solid to obtain 1.9 g of a dry product. After dissolving this dry product in methanol and passing through a LiChrolut RP-18 solid-phase extraction column, the product was applied to chromatography using a reverse-phase HPLC column. As a result of passing through the column at a flow rate of 25 ml/min at 40° C. using 80% aqueous methanol containing 50 mM ammonium acetate, 431 mg of orniplabin were obtained from the fraction that eluted during a retention time of 34 to 39 minutes.

(3) Administration of Orniplabin

After administering carbon tetrachloride for 6 weeks, the animals were divided into an orniplabin dose group and control group so as to be statistically equivalent (orniplabin dose group: 7 animals, control group: 6 animals). Orniplabin was continuously administered into the abdominal cavity at 10 mg/kg. The control group was continuously administered physiological saline into the abdominal cavity at 2 ml/kg. This procedure was carried out for 14 days.

Following completion of administration, blood samples were collected from the vena cava into a syringe barrel containing anticoagulant in the form of 3.8% sodium citrate solution (1/10 volume of collected blood), and the resulting blood was centrifuged immediately for 20 minutes at 3000 rpm to collect the supernatant for use as blood samples.

(3) Measurement of Plasma Parameters

The levels of AST (aspirate aminotransferase, GOT), ALT (alanine aminotransferase, GPT) and ChE (cholinesterase) were measured for the resulting blood samples (Hitachi Model 7180 Autoanalyzer).

Figure 3:
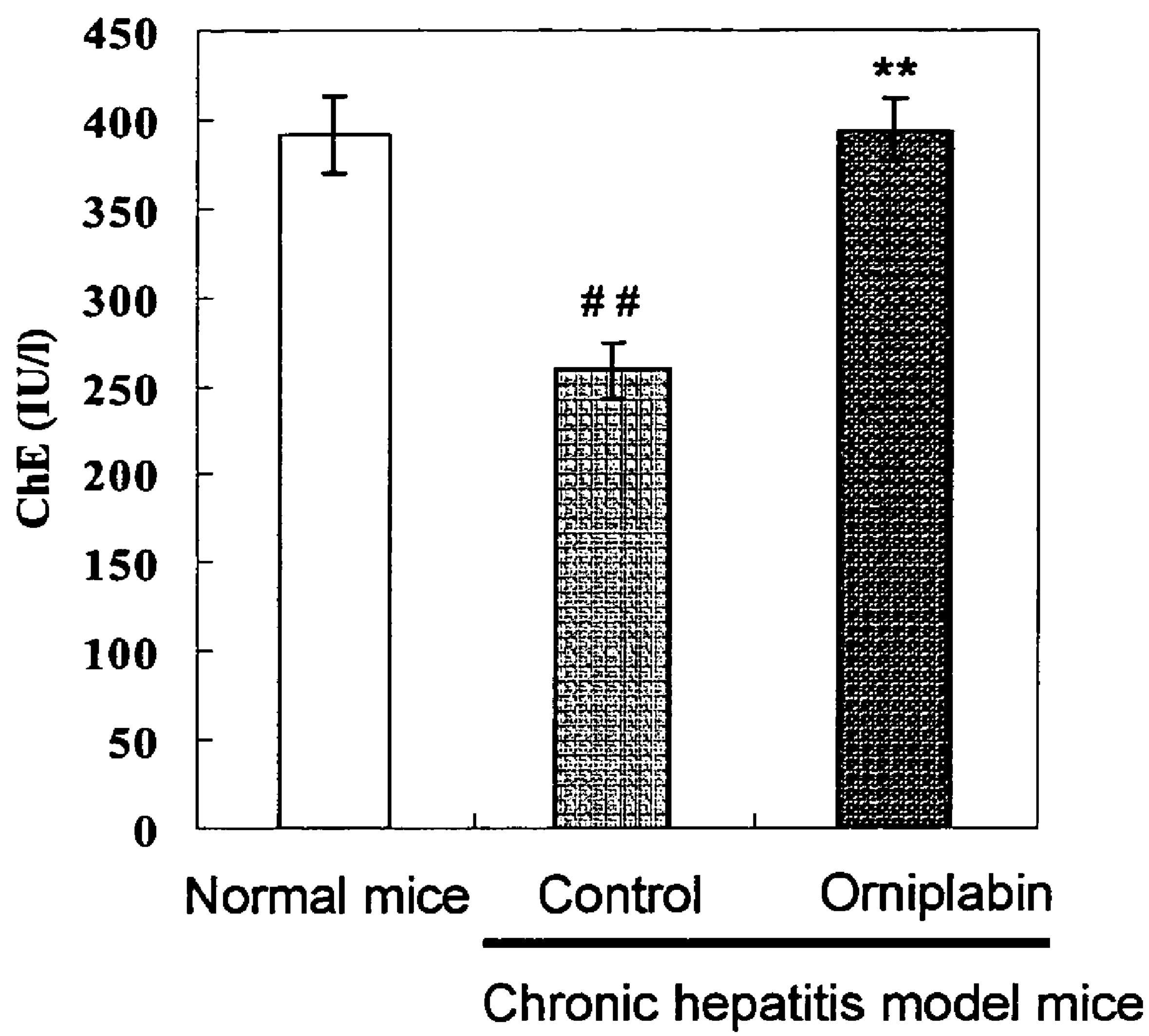
FIG. 3 shows the results of measuring plasma ChE. The symbols in the figure are the same as defined for FIG. 1.

A significant ($P<0.01$) decrease in AST was observed in the orniplabin dose group as compared with the control group (FIG. 1). A significant ($P<0.01$) increase in ChE was observed in the orniplabin dose group as compared with the control group, while a significant ($P<0.01$) decrease was observed in the control group as compared with the normal group (FIG. 3).

Figure 2:
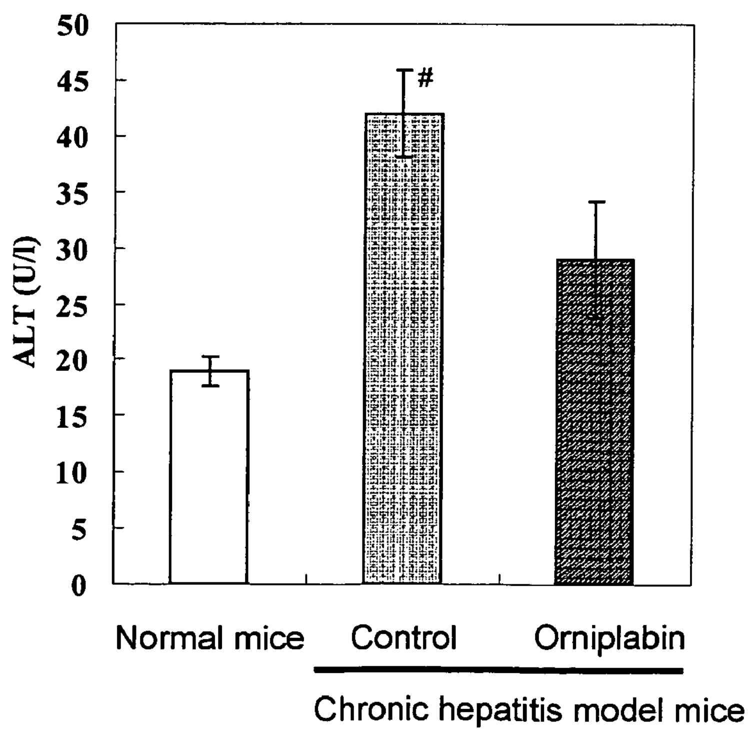
FIG. 2 shows the results of measuring plasma ALT. The symbols in the figure are the same as defined for FIG. 1.

Although there were no significant differences observed for ALT between the orniplabin dose group and the control group, decreases in ALT levels attributable to administration of orniplabin were observed. In addition, although a significant ($P<0.01$) increase was observed in the control group as compared with the normal group, increases were not observed in the orniplabin dose group (FIG. 2).

On the basis of important parameters for representing impaired liver function in the form of AST and ALT, the degree of impaired liver function was indicated to recover to nearly the normal level as a result of administration of orniplabin, and since cholinesterase levels, which indicate the protein synthesis ability of the liver, also recovered to the same level as the normal level, liver function can be said to have a tendency to recover.

The invention claimed is:

1. A method for improving liver function comprising:
administering a therapeutically-effective amount of purified orniplabin (SMTP-7) to a patient in need thereof, wherein said patient suffers from hepatitis.

2. The method according to claim 1, wherein orniplabin (SMTP-7) is administered in a dosage of 0.01 to 100 mg/kg of body weight per day.

3. The method according to claim 2, wherein said dosage is administered either once per day or divided into several administrations.

* * * * *